United States Patent [19]

Selman

[11] Patent Number: 5,514,669

[45] Date of Patent: May 7, 1996

[54] USE OF PHOTODYNAMIC THERAPY TO TREAT PROSTATIC TISSUE

[75] Inventor: Steven H. Selman, Toledo, Ohio

[73] Assignee: Medical College of Ohio, Toledo, Ohio

[21] Appl. No.: 128,792

[22] Filed: Sep. 29, 1993

[51] Int. Cl.$^6$ .................. A61K 31/555; A61K 31/695
[52] U.S. Cl. .................. 514/63; 514/184; 514/185
[58] Field of Search .................. 514/184, 185, 514/63; 424/9

[56] References Cited

U.S. PATENT DOCUMENTS

| | | | |
|---|---|---|---|
| 4,589,404 | 5/1986 | Barath et al. | 128/6 |
| 4,740,047 | 4/1988 | Abe et al. | 350/96.15 |
| 4,877,872 | 10/1989 | Morgan et al. | 540/145 |
| 4,988,808 | 1/1991 | Morgan et al. | 540/145 |
| 5,051,415 | 9/1991 | Morgan et al. | 514/185 |
| 5,071,416 | 12/1991 | Heller et al. | 606/3 |
| 5,116,615 | 5/1992 | Gokcen et al. | 424/94.2 |
| 5,166,197 | 11/1992 | Kenney et al. | 514/63 |
| 5,169,395 | 12/1992 | Narciso, Jr. | 606/7 |
| 5,196,005 | 3/1993 | Doiron et al. | 606/7 |
| 5,199,950 | 4/1993 | Schmitt et al. | 604/95 |
| 5,216,012 | 6/1993 | Morgan et al. | 514/410 |
| 5,231,684 | 7/1993 | Narciso, Jr. et al. | 385/80 |
| 5,298,018 | 3/1994 | Narciso, Jr. | 604/21 |
| 5,322,507 | 6/1994 | Costello et al. | 128/4 |
| 5,330,741 | 7/1994 | Smith et al. | 424/9 |

FOREIGN PATENT DOCUMENTS

WO92/10142  6/1992  WIPO .

OTHER PUBLICATIONS

Loh et al., Endogenous porphyrin distribution induced by 5-aminolaevulinic acid in the tissue layers of the gastrointestinal tract, J. Photochem. Photobiol., 20:47–54, 1993.

P. Sekher et al., Spectroscopic Studies of Tin Ethyl Etiopurpourin in Homogeneous and Heterogeneous Systems (1993), J. Photochem. Photobiol. B: Biol, 20:117–125.

International Search Report, Medical College of Ohio, PCT/US/94/07755, fld. 8 Jul. 1994.

Martinetto et al., Bactericidal Effects Induced By laser Irradiation and Haematoporphyrin Against Gran–Positive and Gran–Negative Microorganisms, Drugs Exp. Clin. Res. XII(4), 335–342, (1986).

Selman et al., Copper Benzochlorin A Novel Photosensitizer For Photodynamic Therapy: Effects On A Transplantable Urothelial Tumor, Photochem. and Photobiol., 57:681–685 (1993).

Morgan et al., Observations on the Synthesis and Spectroscopic Characteristics of Purpurins, J. Org. Chem. 51:1347–1350 (1986).

Skalkos et al., Iminium Salt Benzochlorins As Potential Photosensitizers In Photodynamic Therapy, Med. Chem. Res. 2:276–281 (1992).

Windahl et al., Photodynamic therapy of localised prostatic cancer, The Lancet 336:1139, (Nov. 3, 1990).

Selman et al., Normal Tissue effects of the metallopurpurin SnET2 and light. Proceedings of the International Society for Optical Engineering. SPIE 997:12–17, 1988.

Selman et al., Jejunal blood flow after exposure to light in rats injected with hematoporphyrin derivative. Cancer Res., 45:6425–6427, 1985.

Chaudhuri et al., Morphological changes of tumor microvasculature following hematoporphyrin derivative sensitized photodynamic therapy, Photochem. and Phtobiol., 46(5):823–827, 1987.

Selman et al., Hemodynamic effect of the metallopurpurin SnET2 and light on transplantable FANFT–induced tumors, J. Urology, 143:630–633, 1990.

Baert et al., Transuretharal microwave hyperthermia for benign prostatic hyperplasia: Preliminary clinical and pathological results, J. Urology, 144:1383–1387, 1990.

Primary Examiner—Allen J. Robinson
Assistant Examiner—Mary C. Cebulak
Attorney, Agent, or Firm—Emch, Schaffer, Schaub & Porcello Co.

[57] ABSTRACT

The present invention provides a method for diagnosing or treating prostatic tissue in a human or animal patient which comprises sensitizing the prostatic tissue with an effective amount of a photosensitive composition which accumulates in the prostatic tissue and exposing the sensitized tissue to a source of light energy for a predetermined time and intensity sufficient to cause cellular and/or tissue function of the sensitized prostatic tissue to diminish or cease.

12 Claims, 2 Drawing Sheets

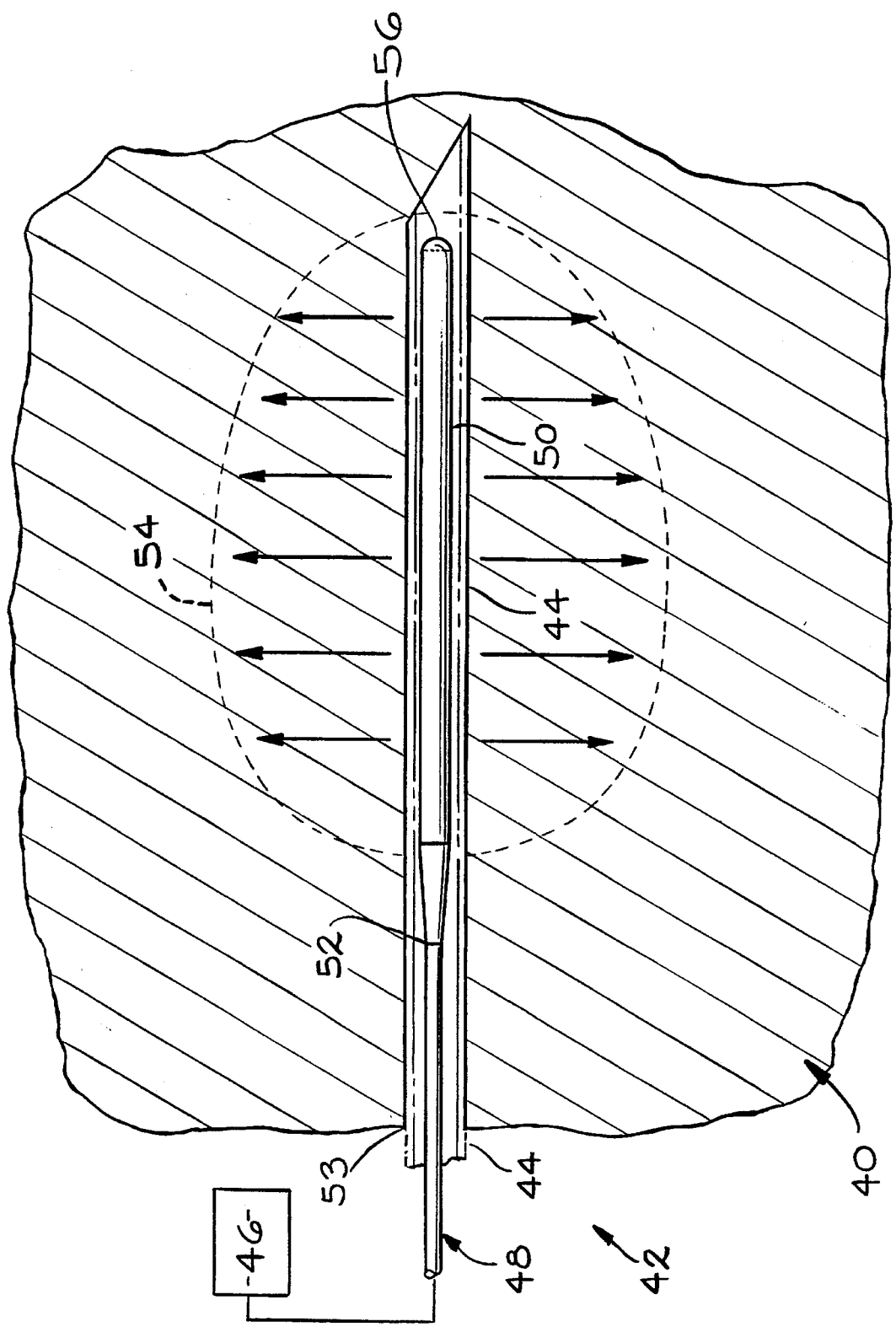

USE OF PHOTODYNAMIC THERAPY TO TREAT PROSTATIC TISSUE

BACKGROUND OF THE INVENTION

This invention relates generally to the medical field and, more particularly, to the use of photodynamic therapy to treat prostatic tissues, and to the use of transurethral photodynamic therapy to treat malignant transformation of the prostate tissue, such as obstructive carcinoma of the prostate and inflammatory conditions of the prostate. The present invention involves treatment of a patient with prostatic disorders using a photosensitive composition which accumulates in the prostatic tissue.

Various types of prostatic tissue become hypertrophied or increased in size, which increase does not necessarily involve malignant transformation. While the causes of such hypertrophy of the tissue are numerous, until the present invention, the treatments of such hypertrophied tissue have various limitations. In particular, benign prostatic hypertrophy (BPH) causes enlargement of the prostate gland and/or constriction of the urethra. Benign prostatic hypertrophy is a relatively common disorder in older males. Another type of prostate disorder is cancer of the prostate, such as obstructive carcinoma of the prostate. Still another type of prostate disorder is prostatitis. Prostatitis is an inflammatory condition due to an infective pathogen, such as a bacterium or other microbe. Often prostatitis does not respond well to antibiotic treatment. In chronic or severe cases of prostatitis, abscesses can form and destroy prostatic tissue. Some manifestations of these prostate disorders cause a constriction of the urethra within the prostate and results in various symptoms including stanguria, nocturia, frequency of urination and sometimes retention of urine.

Currently there are various methods for treating prostatic disorders including surgical treatment, drug therapy, hypothermia and hyperthermia treatment, implantation of prostatic stents and enlargement of the urethra using dilation balloons.

The surgical treatment of these disorders involves exposing the prostate and removing the affected prostatic tissue under direct vision by the surgeon. Another surgical method involves transurethral resection wherein an instrument is placed in the external opening of the urethra and sections of the prostate gland are removed from within the prostatic urethra. Despite the significant advances in patient treatment using transurethral resection, there is a need for less invasive treatment to relieve the patient of the symptoms of such prostate disorders. It is widely known that complications including bleeding, infection, residual urethral obstruction or stricture, retrograde ejaculation, incontinence or impotence may result from these surgical methods.

One partially effective method in achieving urinary outflow involves the placement of a tube or catheter through the external urethra into the bladder in order to allow urine to flow from the bladder. The urinary catheter may have a balloon at the distal tip which, when inflated within the bladder, prevents the removal of the catheter from the body. This method generally is not a suitable long term treatment since problems from infection and maintenance of the catheter may arise.

Other attempts to treat prostatic disorders involve dilation of the urethra in an area adjacent the prostate gland. Various methods of dilation have been proposed in order to enlarge the urethra to allow for normal urination. One continuing concern is that the prostate gland returns to its original dimensions after dilation. Thus, the dilation provides only a temporary solution to the urethral constriction. The fibrous prostate gland is resilient and causes constriction of the urethra to recur shortly after treatment. This is of particular concern since prostatic disorders involve the fibrous and enlarged tissue of the prostate gland itself. Enlargement by dilation of the urethra wall typically has no lasting effect on relieving the constriction on the urethra since the prostate gland returns to its previous shape shortly after dilation.

Therefore, it is important that a method for treating prostatic disorders include a way to keep the urethra from being constricted by the prostate gland after such treatment. Without such treatment, the patient may be required to undergo repeated treatments in order to maintain the integrity of the urethra lumen.

In photodynamic therapy photosensitive compositions are used to selectively destroy pathologic tissue. For example, various photosensitive compounds localize in tumorous tissue where the compositions absorb light at certain wavelengths when irradiated. The photosensitive compositions are useful due to their ability to localize in the cancerous or tumorous tissue and not in the surrounding non-canoerous or normal tissues.

Photosensitive compositions have been proposed as useful compounds for topical application for diagnosis and treatment of skin diseases. In addition, photosensitive compositions have been proposed for use to sterilize biological samples containing infectious agents such as bacteria and viruses. The bactericidal effects are induced by irradiation of tissues treated with photosensitive compositions against gram-positive and gram-negative microorganisms (Martinetto et al. Drugs Exp. Clin. Res. XII (4) 335–342, 1986). The photosensitive compositions have also been used to decontaminate blood and blood components. In addition, photosensitive compositions have been used in the treatment of blood vessel occlusions such as atherosclerotic plaques, thrombi, and the like.

Photodynamic therapy in combination with hyperthermia has also been proposed as a useful method in treating many of these applications. Photosensitive compositions have also been proposed as useful in the diagnosis of disease. These photosensitive compositions have fluorescent properties and since the photosensitive compositions sequester in diseased tissue, fluorescent measurement can be used to diagnose and localize the disease, or direct therapy.

Until the present invention there has been no suggestion of using photodynamic therapy, either alone or in combination with hyperthermic therapy, in the diagnosis and treatment of noncancerous, prostatic disorders, such as benign prostatic hypertrophy and prostatitis.

Further, until the present invention, there has been no suggestion of using photodynamic therapy in the in vivo treatment of an infectious prostatitis.

DISCLOSURE OF THE INVENTION

The present invention provides a method of diagnosing and treating prostatic disorders and the related symptoms of urinary retention or urinary frequency, The method of the present invention requires little or no hospitalization and avoids the possible complications which accompany other methods of treating prostatic tissues. In one embodiment, the present invention provides a method for relieving the constriction of the urethral opening or lumen. The present invention further provides a method for treating prostatic disorders which method comprises destruction of photosensitized prostate tissue using photodynamic therapy either alone or in combination with hyperthermic therapy.

It is contemplated that various photosensitive compositions are useful in the present invention. There are various classes of useful photosensitive compositions, including, for example, porphyrins, chlorins (such as benzochlorins, benzochlorin metal complexes, bacteriochlorins and the like), purpurins, verdins, phthalocyanines and iminium salts of these compositions and other compositions. It is to be understood that the present invention envisions the use of these and other classes of photosensitive compositions, and the present invention is not limited to particular photosensitive compositions.

Examples of various known photosensitive compositions include those compounds disclosed in Selman et al., Photochem. and Photobiol., 57:681–685 (1993), Morgan et al., J. Org. Chem. 51:1347–1350 (1986), Skalkos, et al., Med. Chem. Res. 2:276–281 (1992), the U.S. patent application Ser. No. 07/901,597 and Morgan, et al., U.S. Pat. Nos. 4,877,872, 4,988,808, 5,051,415 and 5,216,012 references, which are expressly incorporated herein. (All references disclosed herein form a part of the disclosure and are expressly incorporated by reference.) These compositions are physiologically acceptable for subcutaneous or intravenous administration as solutions, emulsions or suspensions or for topical, rectal or oral preparations.

The photosensitive composition is administered in an effective amount such that a sufficient amount of the photosensitive composition accumulates in the prostatic tissue. In certain embodiments of the present invention, a predetermined period of time is allowed to pass in order to optimize the accumulation of the photosensitive composition in the affected tissue. It is contemplated that various protocols of treatment using the method of the present invention may involve illuminating the photosensitive compositions for time periods ranging from a relatively short time of approximately one hour or less to a longer time of three to four days after administration of the composition to the patient. However, it should be understood that the optimum time lapse (if any) between drug administration and illumination depends on the type and amount of photosensitive composition administered, the patient's history and the judgment of the practitioner.

After the photosensitive composition accumulates in the tissue, the tissue is irradiated with light of a predetermined wavelength at which the composition shows absorbance peaks optimum for fluorescence excitation or, using another wavelength, for tissue destruction. This absorption of light energy by the photosensitive composition causes a reaction which destroys the tissue in which the composition has accumulated and the light is delivered. It is to be understood that the particular wavelength and intensity of light energy delivered to the tissue is dependent, in part, upon the type of photosensitive composition being used. In certain embodiments, photosensitive compositions which have absorbance peaks at longer wavelengths and show greater absorbencies may be used. In various embodiments, the longer wavelength peaks are advantageous because the light of the longer wavelengths is capable of greater penetration of tissue, while the greater absorbencies are desirable because less light energy is required to cause a given degree of reaction.

In addition to the required photosensitive composition, certain additional components may be chemically attached to or physically combined with the photosensitive composition for administration to the patient. These additional components may include labeling compositions including, for example, cytotoxins, monoclonal antibodies and receptor ligands, which may enhance the photosensitive composition's selectivity for the prostate.

The photosensitive compositions and any additional components are formulated into a final pharmaceutical formulation for administration to the patient using techniques generally known in the art. The pharmaceutical formulation can be administered systemically, in particular by intravenous injection and can be used singly or as components of mixtures as solutions, emulsions or suspensions. The pharmaceutical formulation may be delivered orally, topically, intravenously, subcutaneously, rectally, or by direct injection into the tissue. For example, in one embodiment of the invention, the photosensitive composition is delivered by direct injection into the prostate via a transurethral, transrectal or transperineal approach. It is to be understood that the injectable materials can be prepared in conventional forms either as liquid suspensions or solutions, solid forms suitable for solution or suspension and liquid prior to injection or as emulsions. The formulation may include suitable excipients such as saline, dextrose, glycerol, water and the like. The injectable formulation may also contain additional components such as pH buffering agents, wetting or emulsifying agents and the like. Various modes of administration are well known in the art and the systemic administration can be implemented in a manner which is most suitable for delivery of the photosensitive composition. This administration can include a slower sustained release system or, if properly formulated, an oral administration. The quantity of the formulation being administered is dependent upon the choice of the active photosensitive composition, the condition to be treated, the mode of administration, the individual patient and the expertise and judgment of the practitioner. As such, smaller or larger doses may be needed depending upon the specificity of the formulation. It is contemplated that in formulations having such additional components such as highly specific monoclonal antibody preparations and specific receptor ligands, the dosages may be less than formulations which are less specific to the target tissue. It is contemplated that ranges in about 0.05–10 mg/kg are suitable. It is to be understood that these ranges are merely suggestive and many variables must be taken into consideration in the treatment of individual patients and variations from these recommended values are expected.

The wavelength of irradiating light is chosen to match the maximum absorbance of the photosensitive composition. The suitable wavelengths for the photosensitive compositions are readily determined by the composition's absorption spectrum. For example, the photosensitive composition tin (II) chloride etiopurpurin is illuminated with light that includes the absorption peak at 660 nm. The irradiation dosages are readily determined and dependent upon the method of delivery of the photosensitive composition (i.e. intravenous, topical administration, direct injection and the like) and the type and amount of photosensitive composition being administered. Thus, the intensities of light illumination will typically be in the range of less than about 15 to more than about 500 joules of light.

Other ingredients which can be included in the formulation include antimicrobial agents and/or preservatives as necessary. Many variations of the above, along with other suitable vehicles will suggest themselves to those skilled in the art in light of the description herein.

Irradiation of the tissue containing the photosensitive composition in accordance with the instant invention can be achieved by delivering light energy from conventional light source, or a laser, or by sending an electromagnetic signal from an appropriate transmitting device. The particular method of irradiation of the tissue depends upon the location in the patient of the affected prostatic tissue.

The light energy can be delivered through a light delivery means via a transurethral, transrectal or transperineal approach. It is also contemplated that the light can be delivered by direct insertion of a light delivery means into the prostatic tissue. For example, in one embodiment, the light energy is delivered through an optical fiber which can optionally have a light diffusing means operatively attached thereto. Another embodiment of the present invention also provides for delivery of light to the prostate via a transurethral approach.

In one particular embodiment, the light energy is delivered to a patient's prostate by placing the light delivery means in a urethral catheter. The light delivery means is properly located within the urethra and positioned adjacent to the target prostate tissue. A portion of the catheter is sufficiently transparent or translucent to allow the light energy to adequately irradiate the adjacent prostatic tissue. In various embodiments of the present invention, a balloon may be affixed to the distal end of the catheter for fixation of the balloon within the bladder and adjacent the bladder sphincter muscle. In various embodiments of the present invention, it is also possible to affix a second balloon coaxially around the catheter. The distal end of the second balloon adjacent the distal end of the catheter may be coated with an opaque or reflective shield type material such that light does not penetrate the adjacent sphincter muscle or bladder tissues. It is also contemplated that an opaque and/or reflective stop means can be positioned adjacent the distal end of the catheter to prevent the light delivery means from entering the sphincter or bladder. The stop means also aids in confirming proper localization of the catheter.

It is also contemplated that the catheter can be provided with an apparatus to cool or heat the affected tissue area. It is also contemplated that the catheter can be provided with various means for guiding the catheter through a lumen, and means for measuring light intensity, temperature and drug fluorescence or illumination. It is also contemplated that the catheter can be provided with an irrigation apparatus to provide a source of irrigation to the area as desired and to keep the area being irradiated relatively clear.

Accurate positioning of the light delivery means assures that there is limited penetration of light into the tissue and that only the desired tissue is irradiated. Such accurate positioning can be aided by using an ultrasound probe. It is also contemplated that other methods of accurately positioning the light delivery means can be used. For example, the catheter and/or light delivery means can have graduated marks thereon so that the actual position of the light delivery means can be accurately located.

The light delivery means can be in the form of a light guide, such as a fiber optic bundle, which in preferred embodiments, comprises at least one optical fiber having an appropriate provision for lighting thereof. The light delivery means and catheter each have a sufficiently small cross section so that the light delivery means and catheter may be fabricated within the appropriate dimensions to comfortably fit within the patient's body or desired orifice. The catheter may be of a rigid type material or may be made of sufficiently flexible material for positioning the light delivery means and catheter throughout a tortuous path.

If desired, the light energy may be delivered interstitially into the prostatic tissue by first inserting a needle into the prostatic tissue via a transurethral, transrectal or transperineal approach. The light delivery means is coaxially inserted through the needle and the needle is thereafter removed, leaving the light delivery means directly in contact with the affected prostatic tissue.

After proper localization of the light delivery means is achieved, the light source is operatively engaged and light energy irradiates the adjacent tissue. The preferred length of time of irradiation and wavelength of light are determined by the type and amount of photosensitive composition being used and other factors as described above. The irradiation of the photosensitive composition causes the photosensitive composition to absorb light generally or induces a photochemical reaction of the photosensitive composition, thereby inducing destruction of the affected tissue. The photosensitive composition may cause a hemorrhagic necrosis of the affected tissue. Further, with the passage of time there is subsequent diminishment or cessation of the cellular and/or tissue functions and subsequent atrophy of the prostatic tissue. It is surprisingly found that when using a transurethral approach, the urethra itself and the urethra mucosa are either spared any damage or regenerate while the tissue of the prostate gland remains in the destroyed or atrophied state.

Further objects, features and advantages of the present invention will become apparent from the detailed description of the preferred embodiments which follows, when considered together with the attached Figures.

BRIEF DESCRIPTION OF THE DRAWINGS

FIG. 2 is a simplified sectional view of a region of a patient's prostatic tissue, schematically illustrating another method of practicing the present invention.

DETAILED DESCRIPTION OF THE PREFERRED EMBODIMENTS

Figure 1:
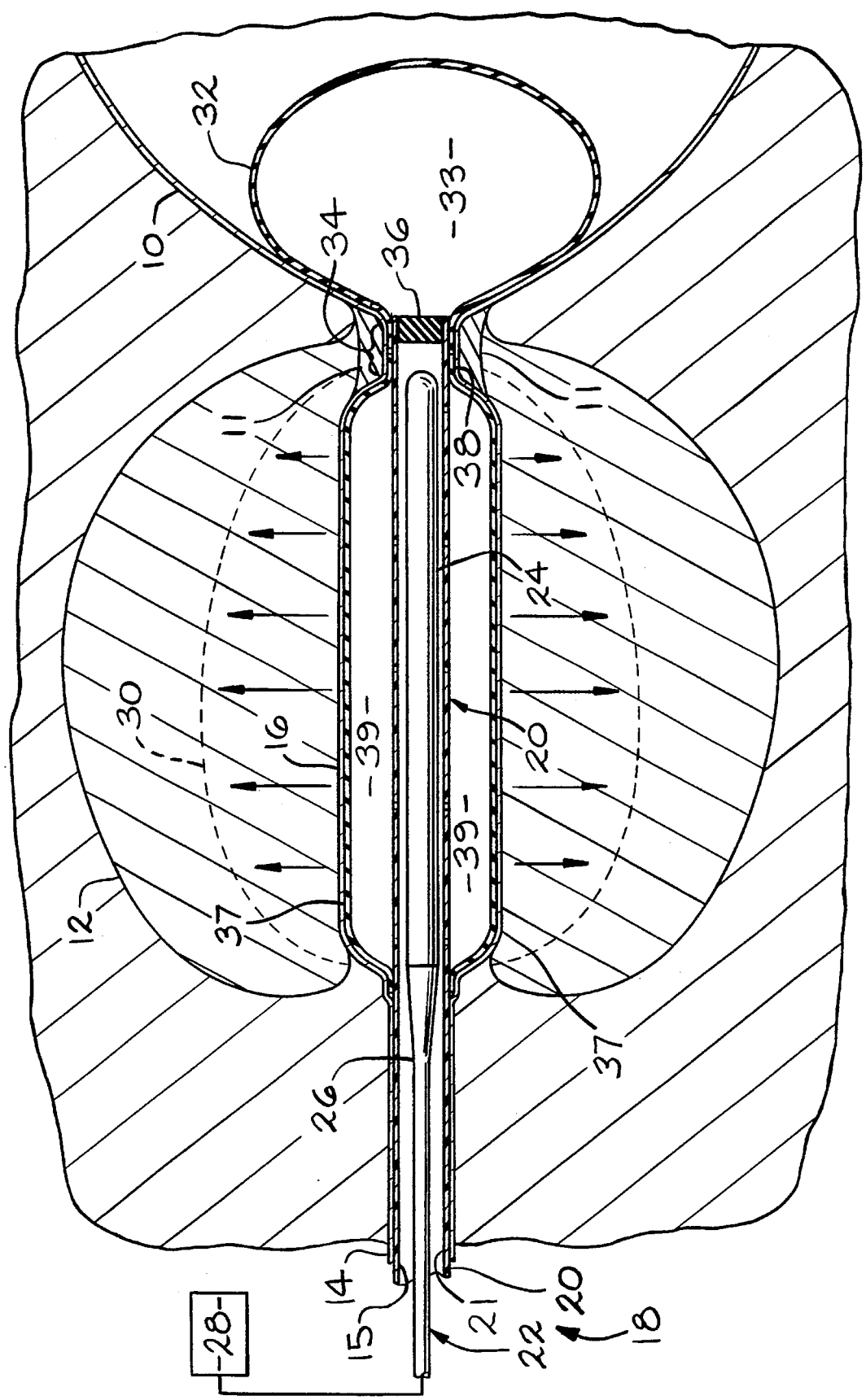
FIG. 1 is a simplified sectional view of a region of a male showing the urethra, prostate gland and bladder, schematically illustrating one method of practicing the present invention.

Referring to FIG. 1, there is illustrated in simplified form a sectional view of a male showing a bladder 10 (including the bladder sphincter muscle 11), a prostate gland 12, a urethra 14 in a distended condition and defining an opening or lumen 15 and a prostatic portion 16 of the urethra 14 extending through the prostate 12. It is the prostate gland 12 which causes constriction or stenosis of the prostatic urethra 16. It is to be understood that in various prostatic disorders, the interior diameter of the prostatic urethra 16 has become smaller than the interior diameter of the non-prostatic urethra 14. In FIG. 1, the diameter of the prostatic urethra 16 is drawn slightly out of proportion and is enlarged for ease of illustration of the present invention.

A photodynamic therapy system or apparatus 18 in accordance with one embodiment of the present invention is generally shown in FIG. 1. The photodynamic therapy apparatus 18 generally comprises a catheter 20, a light delivery means 22 and a source of light energy 28. The catheter 20 defines an opening 21 extending axially therethrough for receiving the light delivery means 22. The light delivery means 22 can comprise at least one, or alternately multiple, long, small diameter optic fibers. The light delivery means 22 coaxially extends through the catheter 20. In a alternative embodiment (not shown), the light delivery means 22 may be a part of the catheter 20. It is to be understood that the catheter 20 and the light delivery means 22 may generally have a rounded or tapered configuration to minimize any damage to the urethral lining and to ease insertion of the catheter 20 and light delivery means 22 into the opening 15 of the urethra 16. At least a portion of the catheter 20 is disposed within the prostatic urethra 16. The light delivery means 22 has a distal end 24 which is generally transparent or translucent and a proximal end 26 which extends from the distal end 24 out of the patient's body to the light energy or optical signal generating source 28 such as a laser, LED device, or lamp.

It has been found that one particularly useful light source comprises a laser which delivers highly accurate intensities and wavelengths of light through at least one optical fiber with a distal end which is comprised of a diffusing material which allows the light to radiate from the optic fiber. For example, useful light sources are described in U.S. Pat. Nos. 5,169,395 and 5,196,005.

The proximal end 26 of the light delivery means 22 is preferably of an opaque and/or reflective material such that no light is delivered to any surrounding tissue. The axial length of the distal end 24 is sufficient to generally illuminate an affected area 30 of the prostate 12. In preferred embodiments, the length of the distal end 24 can vary from about 1 to about 4 cm., depending upon the extent of the obstruction of the urethra and the size of the prostate gland itself. It is understood that the preferable length of the distal end 24 will vary from patient to patient and that judgment of the practitioner will determine the proper length of the distal end 24 in order to accurately deliver the required light to the prostatic tissue. In certain embodiments, it is preferred that the distal end 24 be of a diffusing material such that the light radiates outwardly from the axis of the distal end 24 into the prostate 12. In the embodiment shown in FIG. 1, the affected area 30 of the prostate 12 receives the diffused light (schematically indicated with arrows) which passes through the catheter 20, a balloon 37 and the prostatic urethra 16 into the affected area 30 of the prostate 12.

In certain embodiments, it is contemplated that a flexible, resilient balloon 32 can be positioned on a distal end 34 of the catheter 20. The balloon 32 can be positioned snugly adjacent the bladder 10 and sphincter muscle 11. The balloon 32 aids in positioning the catheter 20 and the light delivery means 22 and protects the adjacent tissues. The balloon 32 is filled (in certain embodiments, under pressure) with a suitable fluid, such as air or a saline solution material 33 and is sealed. The distal end 34 of the catheter is preferably made of opaque and/or reflective material which prevents the light from penetrating or scattering into the sphincter muscle 11, bladder tissue 10 and surrounding tissues. It is also contemplated that the balloon 32 can be of an opaque or reflective material.

Also, an opaque and/or reflective type stop means 36 can be positioned between the balloon 32 and the distal end 34 of the catheter 20 to provide a further safeguard against positioning of the distal end 24 of the light delivery means 22 beyond the point of the affected prostatic tissue and to further prevent light from penetrating or scattering into the surrounding tissues.

It is also contemplated, in certain embodiments, that a second flexible, resilient balloon 37 may be coaxially placed around the catheter 20 such that the second balloon 37 is positioned within the prostatic urethra 16 adjacent the prostatic tissue. The second balloon 37 is of a generally transparent or translucent material which allows the light to pass therethrough. A distal portion 38 of the balloon 37 is coated with a suitable light absorbing and/or reflective material to prevent the light from penetrating or scattering into the surrounding tissues. The balloon 37 is filled (in certain embodiments, under pressure) with a transparent or translucent material 39 such as air, saline solution, water, or other suitable fluid and is sealed. The second balloon 37 may be used to smooth out any invagination of the prostatic urethra 16 and surrounding prostate tissue such that when the prostate is irradiated, there is a more even delivery of light into the affected area 30 of the prostate 12. The second balloon 37 can also be used to help localize and hold the catheter 20 in position within the prostatic urethra 16.

The various methods and apparatuses used to deliver the material 33 to the first balloon 32 and the transparent or translucent material 39 to the second balloon 37 are operatively connected to the device of the present invention, but not shown for easier visualization of the invention. It is also contemplated that monitors (not shown) can be placed in the balloon walls (not shown) for measuring light intensity and temperature. This positioning of the catheter 20, balloons 32 and 37, and light delivery means 22 can be aided using an ultrasound probe (not shown) and/or by direct visualization using an endoscope (not shown).

It is to be understood that, in certain embodiments, while the first balloon 32 and second balloon 37 are provided for ease and safety of use, they are not essential to every embodiment of the method of the present invention and may be eliminated without departing from the spirit and scope of the present invention.

Also, it is contemplated that various other apparatuses (not shown) may be employed within the scope of the present invention in order to ease the use of the method of the present invention by cleansing, heating and/or cooling the tissue being treated with the photodynamic therapy of the present invention. For example, low level hyperthermic treatment of the prostatic tissue, when used with the photodynamic therapeutic method of the present invention, shows a strong synergistic reaction. In particular, when about 40°–45° C. heat is delivered to the tissue by, for example, microwave (not shown) or laser (not shown), the effects of the photodynamic therapy are enhanced.

After the light delivery means 22 is localized adjacent the prostate 12, the light source 28 is activated and light energy is delivered to the affected prostatic tissue 30. The intensity, wavelength and duration of the light are dependent upon many variables including the type and amount of photosensitive composition used. During this irradiation, it is possible to continuously monitor the position of the distal end 24 of the light delivery means 22 such that there is little damage to the surrounding tissues. After irradiation, the pressurized fluids 33 and 39 in the first balloon 32 and second balloon 37, respectively, are removed and the catheter 20 and light delivery means 22 are removed from the urethra 14.

Referring now to FIG. 2, there is illustrated in simplified form a sectional view of a patient's prostate generally showing tissue 40, which comprises prostate tissue needing the photodynamic therapy of the present invention. An alternative photodynamic therapy apparatus 42 generally comprises a needle 44 a light source 46, a light delivery means 48 having a transparent or translucent distal end 50 and an opaque proximal end 52. It is contemplated that the distal end 50 can be made of a light diffusing material, such that the light radiates outwardly from the axis of the distal end 50 into the tissue 40. It is also contemplated that an opaque and/or reflective material 56 can be coated onto the end of the light delivery means 48 to prevent light from penetrating beyond the desired tissue area. The needle 44 is inserted into the tissue 40 and causes an opening 53 in the tissue 40. The light delivery means 48 is coaxially inserted into the needle 44 to a predetermined point. The needle 44 is removed (not shown) leaving the light delivery means 48 in direct contact with the tissue 40 (not shown). The light source 46 is activated and light energy is delivered to an affected area 54 of tissue. The affected area 54 of the tissue 40 receives the light (schematically indicated with arrows) from the distal end 50 of the light delivery means 48. Thereafter, the light delivery means 48 is removed from the affected tissue 54 via the opening 53 in the tissue 40.

The following examples are intended to illustrate the present invention but not to limit its scope.

EXAMPLES 1 and 1b

Animals: Adult mongrel dogs were used in all experiments. Dogs were housed 1/cage and given water and canine chow (Purina Chow, Ralston Purina Corp.) ad libitum.

Photosensitive composition: The photosensitizer, tin ethyl etiopurpurin was used. The photosensitizer was administered in anesthetized (xylazine/ketamine) dogs as an emulsion via antecubital vein 24 hours prior to light treatment.

Light source and delivery: An LTI 660 dye laser (PDT Systems, Santa Barbara, Calif.) pumped by a KTP/YAG laser (Laserscope, San Jose, Calif.), was used as a light source. Laser light was delivered to the prostate via a 400 micron optical fiber fitted with a 2.0 cm flexible cylindrical diffuser tip (PDT Systems, Inc., Santa Barbara, Calif.).

EXAMPLE 1a

Example 1 a shows the uptake or accumulation of photosensitive compositions in non-tumorous prostatic tissues.

Photosensitizer extraction: The animals were injected with 1.0 mg/kg of the photosensitizer. Twenty-four hours later, prostate and other tissues were removed from euthanized animals. Tissue samples were removed from the periurethral prostate and the more peripheral regions. Additionally, the mucosa of the urethra was dissected and its photosensitizer content determined. Bladder mucosa and muscularis were also removed. Tissue was weighed and homogenized with a biohomogenizer (Biospec Products, Inc., Bartleville, Okla.) in 3% acetic acid. After homogenization, a 3:1 ethyl acetate:glacial acetic acid mixture was added and mixed vigorously. The sample was then frozen at −20° C. for at least two hours after which it was thawed and saturated sodium acetate added. The ethyl acetate layer, containing the photosensitizer, was removed and its concentration determined using absorbance spectrophotometry (Response II spectrophotomer, Gilford, Oberlin, Ohio).

Tissue Preparation: On removal, the prostates were photographed and then fixed in a 10% buffered formalin solution. After fixation, tissue was sectioned at 5 u intervals and stained with H & E. Sections of the urinary bladder were removed and prepared in a similar manner.

Tissue levels of photosensitizer: Photosensitizer levels were uniform throughout the prostate (1.3+/−0.6 ug/g) as seen in Table 1 below. The urethra and bladder mucosa contained less photosensitizer than prostate (0.3+/−0.1 ug/g, 0.2+/−0 ug/g). Tissue levels of photosensitizer was significantly greater than plasma levels.

TABLE 1

| Tissue Distribution of Photosensitizer | | | | |
|---|---|---|---|---|
| | Dog 1 | Dog 2 | Dog 3 | Mean +/− SD |
| Prostate | 2.1* | 0.8 | 0.9 | 1.3 +/− 0.6 |
| Urethra | 0.5 | 0.3 | 0.2 | 0.3 +/− 0.1 |
| Bladder | 0.2 | 0.2 | 0.2 | 0.2 +/− 0 |
| Liver | — | 6.7 | 6.1 | 6.7 +/− 0.2 |
| Kidney | — | 2.5 | 2.9 | 2.7 +/− 0.2 |
| Spleen | — | 0.8 | 0.8 | 0.8 +/− 0 |
| Muscle | — | 0.3 | 0.2 | 0.3 +/− 0.1 |
| Plasma (24-hr) | — | 0.1** | 0.1 | 0.1 +/− 0 |

*Photosensitizer concentration ug/g
**ug/ml

The tin ethyl etiopurpurin is a hydrophobic sensitizer and it is preferred to administer such composition as an emulsion. Skin photosensitization is not a problem with this photosensitizer.

EXAMPLE 1b

Example 1b shows the photosensitive compositions, which when accumulated in the prostatic tissue, are activated and destroy prostatic tissue upon illumination.

Prostate treatment: The animals were injected with 1.0 mg/kg of the photosensitizer. Twenty-four hours after photosensitizer administration the animals were anesthetized with intravenous sodium barbiturate. The animals were intubated and maintained on a respirator during light treatment. They were treated in the dorsolithotomy position. The 2 cm. diffusing tip of the laser fiber was localized in the prostatic urethra under transrectal ultrasound guidance. A Bruel and Kreuger 7.0 megahertz ultrasound scanner with a transrectal probe was used. The laser fiber was placed within a transparent 10F Stamey catheter (TFX Medical, Duluth, Ga.) which was used as a laser fiber carrier. The tip of the catheter was positioned immediately outside the bladder neck. Once positioned, the prostate was treated with 300 (260 mW/cm$^2$) joules of laser light. The animals were then recovered and returned to their cages. Indwelling catheters were not used after treatment. In two animals the prostate was removed 48 hours after treatment while one had the prostate removed at 3 weeks.

Animal recovery: All animals were able to void spontaneously. Two of the animals developed gross hematuria. Both of these animals showed evidence of damage to the bladder mucosa. One of the animals with hematuria was scheduled to survive three weeks and was placed on prophylactic antibiotic (penicillin/streptomycin) therapy for 8 days.

Prostate effects: The prostates of the animals treated with the photosensitizer and light showed evidence of a photodynamic effect. Prostates removed 48 hours following photodynamic therapy had a dark ring of hemorrhage surrounding the urethra. Histologic examination revealed extensive hemmorhagic necrosis within this area as well as loss of the urethral epithelium. Outside the area of hemorrhagic necrosis, there was glandular atrophy extending in some areas to the capsule of the prostate. The prostate removed 3 weeks following treatment, showed glandular atrophy and replacement with fibrous tissue within an area corresponding to the area of hemorrhagic necrosis seen in the prostate removed at 48 hours. Glandular atrophy was present outside of this area extending in some areas to the capsule. The urethral mucosa had regenerated.

In two of the animals there were extensive changes in the bladder. Grossly the bladder mucosa appeared hemmorhagic and edematous. Microscopically, there was mucosal and submucosal hemmorhage. These changes to the bladder are believed to be due to movement or inaccurate placement of the light guide during treatment.

EXAMPLE 2

The R3327AT prostate tumor model was used in male Copenhagen rats which were injected with 1.5 mg/kg body wt. of SnET2 (tin ethyl etiopurpurin Emulsion, (0.94 mg/ml) PDT Pharmaceuticals). Each rat had one flank tumor (R3327AT). After two weeks, the tumors ranged from 1.0 to 1.6 cm in length. Twenty four hours after TEP injection, the tumor area received photodynamic therapy with a light source of a KTP pumped 660 dye laser (PDT Systems). The KTP/660 dye laser was tuned to 660 nm; power density: 200 mw/cm$^2$; light dose: 0, 200, 300 and 400 Joules. Tumor temperatures were monitored using a 23 gge. hypodermic probe (YSI) placed percutaneously beneath the treated tumor. If needed, the tumors were cooled by a jet of cool air. Tumors were measured and recorded three times per week.

TABLE 2

| Group | Light Dose Joules | Drug Dose (mg/kg) | # of Rats Per Group |
|---|---|---|---|
| I | 0 | 0 | 5 |
| II | 0 | 1.5 | 5 |
| III | 200 | 1.5 | 5 |
| IV | 300 | 1.5 | 5 |
| V | 400 | 1.5 | 5 |
| VI | 400 | 0 | 5 |

The linear regression of tumor growth (represented as tumor volume) for each rat was plotted. The number of days it took the treated tumors to reach their initial tumor volume at the time of treatment was determined by the intercept with a horizontal line drawn at the mean initial tumor volume for all groups. The mean number of days for each light/drug dose group to reach its initial tumor size is recorded in Table 3 below.

TABLE 3

| Group | # of Days of Growth Delay |
|---|---|
| I | 0 |
| II | 0 |
| III | 6.2 +/− 1.2 |
| IV | 5.8 +/− 0.8 |
| V | 11.4 +/− 3.7 |
| VI | 0 |

EXAMPLE 3

The R3327AT prostate tumor model was used in male Copenhagen rats which were injected with 1.5 mg/kg body wt. of SnET2 (Tin Ethyl Etiopurpurin Emulsion, PDT Pharmaceuticals). Each rat had one flank tumor (R3327AT). After two weeks, the tumors ranged from 1.0 to 1.6 cm in length. Twenty four hours (+/−2 hrs.) after SnET2 injection the tumor area received photodynamic therapy using either a 659 YAG or 660 Dye laser fiber optically coupled to a 3-way fiber splitter. The power density was 200 mw/cm$^2$ and the light fluence is shown in Table 4 below.

TABLE 4

| Group | Light Dose Joules | Drug Dose (mg/kg) | # of Rats Per Group |
|---|---|---|---|
| I | 0 | 0 | 5 |
| II | 0 | 1.5 | 5 |
| III | 200 | 1.5 | 5 |
| IV | 300 | 1.5 | 5 |
| V | 400 | 1.5 | 5 |
| VI | 400 | 0 | 5 |

The treatment and control groups were as follows:
Treatment Groups: 1 drug dose and 3 doses at this drug dose, (n=5 rats/group);
Control Groups: No drug/no light and no drug/light (400 J)
Tumor temperatures were monitored using a 23 gge. hypodermic probe (YSI) placed percutaneously beneath the treated tumor. If needed, the tumors were cooled by a jet of cool air. Tumor diameters were measured and recorded three times per week.

Tumor growth was monitored by calculating volumes from the recorded measurements of tumor width, height and length. The rate of growth is presented as the number of days required for an individual tumor to reach 2, 5 or 10 times initial volume. This method of analysis of tumor growth accounts for variations due to differing initial tumor volume (Gibson and Hilf, Cancer Research, 1990). Both lasers were effective in delaying tumor growth from initial to 2 times initial volume as compared to controls, especially at the 400 Joule level. Only at the 200 Joule fluence level was there any significant difference between the YAG and Dye lasers in producing tumor growth delay. There is no consistent significant difference between the 660 Dye and 659 YAG lasers when used as a light source for photodynamic therapy in the R3327AT prostate tumor bearing rats sensitized with SnET2.

It will be appreciated by a person of ordinary skill in the art that while the present invention has been disclosed and described herein with respect to certain preferred embodiments and alternatives thereof, various changes in form and detail may be made therein without departing from the scope and spirit thereof.

I claim:

1. A method for treating the symptoms associated with benign prostatic hyperplasia (BPH) or prostatitis of noncancerous prostatic tissue in a human or animal patient comprising: (a) sensitizing noncancerous prostatic tissue with an effective amount of a therapeutic photosensitive composition with accumulates in the tissue and thereafter (b) exposing the sensitized prostatic tissue to a source of light energy for a predetermined period of time and at a predetermined wavelength, whereby the photosensitive composition in the light-exposed prostatic tissue absorbs the light or undergoes a photochemical reaction.

2. The method of claim 1, in which the prostatic tissue is exposed to the light energy at a predetermined time after the photosensitive composition is administered to the patient.

3. The method of claim 1, which further includes treating the prostatic tissue with hyperthermic therapy.

4. The method of claim 1, in which a light delivery means having a transparent or translucent distal end is positioned adjacent or within the patient's sensitized prostatic tissue prior for delivery of the light energy to the prostatic tissue.

5. The method of claim 4, wherein the source of light energy comprises a laser, LED device or lamp.

6. The method of claim 5, wherein the light energy is delivered to the patient's prostatic tissue by a light delivery means comprising an optical fiber which radially diffuses light.

7. The method of claim 1, in which the photosensitive composition is administered orally, topically, intravenously, subcutaneously, rectally, or by direct injection into the patient's tissue.

8. The method of claim 1, in which the photosensitive composition is administered to the patient in an amount of about 0.05– 10.0 mg/kg of the patient's weight.

9. The method of claim 1, in which the patient's bladder and sphincter muscles are protected from exposure to the light by placing an opaque and/or reflective material at a point beyond the patient's prostate.

10. The method of claim 9, in which the opaque and/or reflective material comprises a portion of a balloon placed within the patient's urethra.

11. The method of claim 1 in which the photosensitive composition destroys benign photosensitized prostatic tissue.

12. The method of claim 1 in which the photosensitive composition comprises at least one composition selected from the group comprising porphyrins, chlorins, purpurins, verdins, phthalocyanines and iminium salts thereof.

* * * * *